United States Patent [19]

Anderson

[11] 4,255,052

[45] Mar. 10, 1981

[54] METHOD OF GENERATING NITROGEN FOR FLAMELESS EMISSION SPECTROSCOPY

[75] Inventor: Robert J. Anderson, Villa Park, Calif.

[73] Assignee: Beckman Instruments, Inc., Fullerton, Calif.

[21] Appl. No.: 78,732

[22] Filed: Sep. 25, 1979

Related U.S. Application Data

[63] Continuation of Ser. No. 921,396, Jul. 3, 1978, abandoned.

[51] Int. Cl.$^3$ .............................................. G01N 21/68
[52] U.S. Cl. ................................. 356/316; 23/232 R; 23/232 E; 422/83; 422/98
[58] Field of Search ....................... 356/311, 312, 316; 23/232 R, 232 E (U.S. only); 422/83 (U.S. only), 98 (U.S. only)

[56] References Cited

U.S. PATENT DOCUMENTS

| 3,242,798 | 3/1966 | Yamamoto | 356/316 |
| 4,148,612 | 4/1979 | Taylor et al. | 356/316 |
| 4,150,951 | 4/1979 | Capelle | 23/232 E |

OTHER PUBLICATIONS

"Analytical Photon Catalysis: Measurement of Gas Phase Concentrations to $10^4/cm^3$" Capelle et al. Applied Physics Letters vol. 30, #8, Apr. 15, 1977, pp. 407–409.

Primary Examiner—Vincent P. McGraw
Attorney, Agent, or Firm—R. J. Steinmeyer; Robert R. Meads; John R. Shewmaker

[57] ABSTRACT

In a system for analyzing the elemental or molecular composition of a sample where the sample components are excited through collision with an active metastable gaseous species, the excited sample components emitting a characteristic wavelength of light which may be detected, the system including a microwave cavity through which the gaseous species flows and a microwave source coupled to the cavity, the microwave discharge exciting the gaseous species, there is disclosed an improved gas and sample introduction system wherein a liquid sample and a water soluble compound are mixed with a diluent and aspirated into the flow, upstream of the microwave cavity, onto a heated filament, the compound being capable of releasing nitrogen or some other suitable gas molecules at high temperature and low pressure whereupon formation of nitrogen and vaporization of the sample occur simultaneously.

10 Claims, 1 Drawing Figure

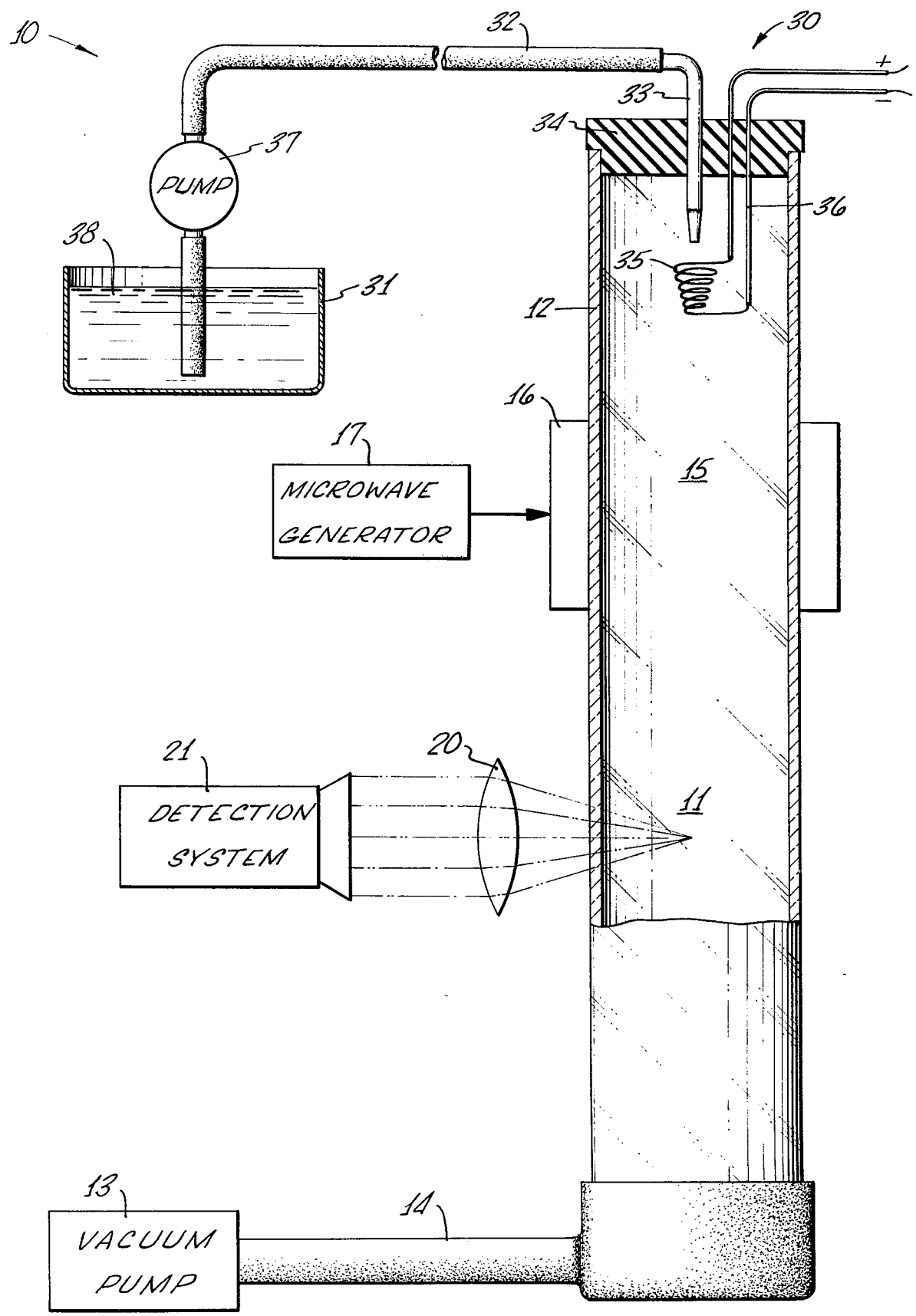

METHOD OF GENERATING NITROGEN FOR FLAMELESS EMISSION SPECTROSCOPY

This is a continuation of application Ser. No. 921,396, filed July 3, 1978, now abandoned.

BACKGROUND OF THE INVENTION

1. Field of the Invention

The present invention relates to flameless emission spectroscopy and, more particularly, to a method of and apparatus for generating nitrogen for use in flameless emission spectroscopy.

2. Description of the Prior Art

A variety of methods and systems exist for the quantitative and qualitative detection and analysis of atomic and molecular species in samples, such as body fluids. One such method and system involves the excitation of the sample atoms through collision with an active metastable gaseous species in a Lewis Raleigh afterglow, the excited atoms then emitting characteristic wavelengths of light as they relax back to their ground state. Specifically, the sample to be analyzed is introduced into a gas stream containing an excess of an active metastable species of nitrogen or other hoble gas whereupon the material, if atomic, is rapidly and repeatedly excited or, if molecular, is decomposed and certain component atoms of the molecule are excited, the excited species emitting characteristic wavelengths of light. The wavelength and intensity of the emitted light are determinative respectively of the identity and concentration of the atoms of the different elements present.

There are at least two advantages to this flameless emission technique. The first of these is that upon relaxation to the ground state, the atoms may collide again with an active nitrogen molecule, providing that the active nitrgen is present in excess, thereby reexciting the atom with a subsequent reemission of a characteristic photon. The second advantage is that in contrast to flame photometry or atomic absorption photometry or other techniques, the background radiation in the Lewis-Rayleigh afterglow region is extremely low in the visible and ultraviolet, permitting the characteristic emission spectra to be observed against a black background. These two advantages combine to make this technique extremely sensitive and capable of extremely good linearity. As a result, a number of systems have been developed utilizing this technique.

The generation of active nitrogen is accomplished in a microwave discharge. Specifically, the technique requires the injection of gaseous nitrogen into a microwave cavity coupled to a microwave generator as well as the mixing of the active nitrogen stream with the sample stream in the vapor phase. A suitable sample introduction system for generating the sample stream in the vapor phase is disclosed in copending patent application Ser. No. 922,938 filed concurrently herewith, entitled Sample Introduction System for Flameless Emission Spectroscopy, and assigned to Beckman Instruments Inc., the assignee of the present application. The sample introduction system of that application, as well as those of other systems, require nitrogen in gaseous form which is typically received from a gas bottle. While providing the gas in this form generally is acceptable, there are circumstances when it is not. Particularly for clinical applications, it is not desirable to have a tank of nitrogen present, simply because of the danger associated therewith. For this reason, clinicians have been reluctant to utilize the flameless emission technique, in spite of its many advantages.

SUMMARY OF THE INVENTION

According to the present invention, there is provided a method and apparatus for generating nitrogen for use in flameless emission spectroscopy which eliminates the necessity for a tank of nitrogen or other gas. In this manner, flameless emission spectroscopy becomes suitable for use in clinical applications. Briefly, it is the teaching of the present invention to add a nitrogen containing, water soluble compound to a suitable diluent, such as water, and to aspirate this solution onto a hot filament in the reaction chamber at reduced pressure. The compound selected would be capable of releasing nitrogen molecules at high temperatures and at reduced pressures. A variety of nitrogen compounds are suitable for this purpose, in particular hydrazine and urea and their respective families of related compounds. In this manner, the nitrogen will be generated internally of the reaction chamber and the clinician will only have to deal with the compound in solid form.

It is therefore an object of the present invention to provide a method of and apparatus for generating nitrogen for use in flameless emission spectroscopy.

It is a further object of the present invention to provide a flameless emission spectroscopic system which eliminates the necessity for a tank of nitrogen or other noble gas.

It is a still further object of the present invention to provide a system for flameless emission spectroscopy in which nitrogen is generated in the reaction chamber by the injection of a water soluble nitrogen containing compound capable of releasing nitrogen molecules at high temperatures and at reduced pressures.

Still other objects, features, and attendant advantages of the present invention will become apparent to those skilled in the art from a reading of the following detailed description of the preferred embodiment constructed in accordance therewith, taken in conjunction with the accompanying drawings wherein:

BRIEF DESCRIPTION OF THE DRAWINGS

The sole FIGURE is a partially schematic, partially sectional side view of a flameless emission spectroscopic system for analyzing the elemental or molecular composition of a sample incorporating a method and apparatus for generating nitrogen in accordance with the teachings of the present invention.

DESCRIPTION OF THE PREFERRED EMBODIMENT

Referring now to the drawing, there is shown a generally known system, designated 10, for flameless emission spectroscopy. System 10 includes a reaction chamber 11 preferably formed from a length of fused silica tubing 12 which is maintained at some low pressure, preferably between 1 and 10 torr, by means of a vacuum pump 13 connected to one end of tubing 12 by a length of rubber tubing 14. The length of tubing 12 is insignificant and the diameter may be approximately 10 mm. A microwave chamber 15 is formed within tubing 12 by surrounding tubing 12 with a microwave cavity 16 which is coupled to a microwave generator 17, the latter preferably operating at 2.45 GHz.

In a conventional system, nitrogen or some other suitable inert gas is fed into chamber 15 where energy is coupled thereto from generator 17, causing the molecules to be raised to an active electronic excited state. The amount of active nitrogen produced is a function of microwave power, pressure, flow rate, and nitrogen purity. If a sample is now forced into the gas phase and mixed with the nitrogen, the material, if atomic, is rapidly and repeatedly excited, or, if molecular, is disassociated into its component atoms and these atoms are rapidly and repeatedly excited. In either case, the atoms present in the sample emit light at specific wavelengths whereupon the wavelengths are determinative of the identity of the atoms and the intensity of the emitted light at each wavelength is determinative of the concentration of the atom present.

At a fixed distance of approximately 5-30 cm downstream of microwave cavity 16, in the area known as the Lewis-Rayleigh afterglow region, the flourescence is monitored to determine the wavelengths and corresponding intensities to establish the identity and concentrations of the elements present. The emitted light may be collected by a collection optics system, generally designated 20, which focuses the light into a detection system 21, that measures the light intensity at the wavelengths of interest.

A typical detection system, known to those skilled in the art, consists of collection lenses, a monochromator, a vidicon detector, and a multichannel analyzer. Optics 20 focuses the light from within chamber 11 onto the input slit of the monochromator. The vidicon detector is located in the focal plane of the monochromator grating, at the normal location of the output slit. The vidicon detector has an array of small photodiodes, each of which therefore views a small portion of the spectrum. The multichannel analyzer displays an output whose amplitude is proportional to the light intensity on each of the photodiodes, resulting in a spectrum of the amplitude of the light intensity as a function of wavelength. Since each of the gaseous species emits light at a specific wavelength, by monitoring the amplitude of the intensity at a specific photodiode, or by summing over several diodes, the concentration of the various species can be determined.

Since the entire spectrum is observed continuously during the passage of the sample through reaction chamber 11, the concentration of a number of different species can be determined simultaneously, from a single sample, during a short period of time on the order of a few seconds to a minute.

System 10 may be advantageously used to analyze various components in body fluids or other liquids. In the case of a liquid sample, it is necessary to introduce the sample into system 10 in such a way that the molecules are completely disassociated into their atomic components and the atomic components completely vaporized. It is also necessary to introduce nitrogen into chamber 15. For both of these purposes, system 10 includes a sample and gas introduction system, generally designated 30.

In sample and gas introduction system 30, a beaker or other reservoir 31 receives one end of a length of tubing 32, the other end of which is connected to one end of a tiny capillary tube 33. Tube 33 is preferably made from a metallic or ceramic material and has a preferred diameter in the range of from 0.001 to 0.01 inches Tube 33 extends through a plug 34 which extends into the end of tubing 12 opposite from the end connected to pump 13. Thus, the other end of tube 33, the tip, extends into tubing 12. A filament 35 is positioned adjacent the tip of tube 33 so that the liquid flowing from tube 33 impinges upon filament 35. The leads 36 from filament 35 extend through plug 34 for connection to a suitable source of voltage. A pump 37 is preferably connected within tubing 32 for pumping liqud 38 from beaker 31 into capillary tube 33.

With the construction just described, the liquid 38 in beaker 31 is aspirated into extremely small droplets by flowing through tube 33, which has a very small diameter. Upon contacting the heated filament 35, the liquid is instantaneously vaporized.

According to the present invention, system 30 is used to introduce nitrogen into chamber 15. Specifically, a chemical compound is added to liquid 38 which is capable of releasing nitrogen molecules upon contact with heated filament 35 and vaporization into chamber 15 at reduced pressure. A variety of nitrogen compounds are suitable for this purpose, in particular hydrazine and urea and their respective families of related compounds. Both hydrazine and urea are water soluble, stable, and easily handled. Both readily decompose at high temperatures, as will be encountered on hot filament 35, and at reduced pressures Both decompose to yield nitrogen molecules, while hydrazine has the additional advantage of acting in aqueous solution as an oxygen scavenger in accordance with the following equation:

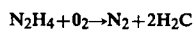

$$N_2H_4 + O_2 \rightarrow N_2 + 2H_2C$$

Other attractive hydrazine related compounds include hydrazine azoimide which is highly desirable due to its high nitrogen content as well as its very high water solubility.

According to the preferred embodiment of the invention, the nitrogen containing compound is diluted in a suitable diluent, such as water, in beaker 31, and this solution is pumped continuously by pump 37 into chamber 15. This provides a constant source of active nitrogen passing into reaction chamber 11. Then, when it is time to run a test, the sample can be added to liquid 38 in beaker 31 and pumped into chamber 15 along with the nitrogen compound.

Evidently, tube 33 and filament 35 must be placed upstream of cavity 16 so that the nitrogen generated when the compound impinges on filament 35 will flow through chamber 15. While the sample under test does not have to be introduced with the nitrogen containing compound, as shown, this is the preferred embodiment since it substantially simplifies the apparatus required for both sample and gas introduction. Futhermore, with the construction shown, the sample is conducted through the discharge in cavity 16. Since the cavity operates at a high frequency, the water in which the sample and the nitrogen containing compound is diluted and the sample itself itself absorb microwave energy and are instantly vaporized. Furthermore, the energy of the discharge causes the sample molecules to become disassociated into their component atoms.

Upon mixing of the sample gas with the active nitrogen in chamber 15, the excited gaseous species collides with the active nitrogen species to excite the gaseous species. Upon relaxation to the ground state, the gaseous species emits a characteristic photon at specific wavelengths. The emitted light is collected by collection optics 20 which focuses the light into detection system 21.

It is desirable to have an excess of nitrogen over sample in the flameless emission technique since this insures that first order kinetics will prevail and that the signal observed will be linearly related to the concentration of the species to be analyzed. It is also desirable to use the sample at very high dilutions, say on the order of 1,000 to 1, since this simplifies the problem of disassociating the sample in the vapor phase. Both of these objectives are met by utilizing hydrazine, urea, or realted compounds at relatively high concentration in the diluent, say on the order of 0.01 to 1 molar, while the sample is injected into the sample chamber at a 1,000 to 1 dilution. Under these condition, the ratio of nitrogen molecules to sample would be in the range of $10^3$ to $10^4$.

It can therefore be seen that according to the present invention, there is provided a method of and apparatus for generating nitrogen for use in flameless emission spectroscopy which eliminates the necessity for a tank of nitrogen or other gas. In this manner, flameless emission spectroscopy becomes suitable for use in clinical applications.

While the invention has been described with respect to a preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

I claim:

1. In a system for analyzing the composition of a sample wherein the sample components are excited through collision with an active metastable gaseous species, the excited sample components emitting a characteristic wavelength of light which may be detected, said system including a chamber through which said gaseous species flows, a microwave cavity coupled to said chamber, and a microwave source coupled to said cavity, said source and said cavity exciting said gaseous species, a method for introducing said gaseous species into said chamber comprising:

dissolving in a suitable diluent a compound which is capable of releasing said gaseous species at high temperature and low pressure;

positioning a heatable element in said chamber, upstream of said mircrowave cavity; and aspirating said diluent with said compound therein into said chamber, onto said heatable element, to generate said gaseous species within said chamber.

2. In a system according to claim 1, wherein said gaseous species in nitrogen, a method wherein: said compound is selected from the group consisting of hydrazine and urea and their related families of compounds.

3. In a system according to claim 1 or 2, a method further comprising:
   dissolving said sample in said diluent for aspiration of said sample into said chamber with said diluent and said compound.

4. In a system according to claim 1, a method wherein:
   said compound is water soluble.

5. In a system according to claim 1, a method wherein said aspirating step comprises:
   aspirating said diluent into said microwave cavity.

6. In a system for analyzing the composition of a sample wherein the sample components are excited through collision with an active metastable gaseous species, the excited sample components emitting a characteristic wavelength of light which may be detected, said system including a chamber through which said gaseous species flows, a microwave cavity coupled to said chamber, and a microwave source coupled to said cavity, said source and said cavity exciting said gaseous species, means for introducing said gaseous species into said chamber comprising:
   a heatable element positioned within said chamber, upstream of said microwave cavity; and
   means for aspirating a diluent into said chamber, onto said heatable element, said diluent having dissolved therein a compound which is capable of releasing said gaseous species at high temperature and low pressure whereby said gaseous species is generated within said chamber.

7. In a system according to claim 6, introducing means wherein:
   said diluent further has dissolved therein said sample.

8. In a system according to claim 6 or 7, introducing means wherein:
   said compound is selected from the group consisting of hydrazine and urea and their related families of compounds.

9. In a system according to claim 6 or 7, gaseous species introducing means wherein said aspirating means comprises:
   a capillary tube, one end of said capillary tube extending into said chamber; and
   means for conducting said diluent into the other end of said capillary tube.

10. In a system according to claim 9, gaseous species introducing means wherein said aspirating means further comprises:
    means for pumping said diluent continuously into said other end of said capillary tube.

* * * * *

UNITED STATES PATENT AND TRADEMARK OFFICE
CERTIFICATE OF CORRECTION

PATENT NO. : 4,255,052
DATED : March 10, 1981
INVENTOR(S) : Robert J. Anderson

It is certified that error appears in the above–identified patent and that said Letters Patent are hereby corrected as shown below:

Column 1, line 25, Delete "hoble" and insert --noble--.

Column 4, line 27, In the formula, delete "C" and insert --O--.

Signed and Sealed this

Twenty-sixth Day of May 1981

[SEAL]

Attest:

RENE D. TEGTMEYER

Attesting Officer   Acting Commissioner of Patents and Trademarks